United States Patent [19]

Edwards et al.

[11] Patent Number: 5,366,490
[45] Date of Patent: Nov. 22, 1994

[54] MEDICAL PROBE DEVICE AND METHOD

[75] Inventors: Stuart D. Edwards, Los Altos; Ronald G. Lax, Grass Valley; Ingemar H. Lundquist, Pebble Beach; Hugh R. Sharkey, Redwood City, all of Calif.

[73] Assignee: Vidamed, Inc., Menlo Park, Calif.

[21] Appl. No.: 172,014

[22] Filed: Dec. 22, 1993

Related U.S. Application Data

[63] Continuation of Ser. No. 929,638, Aug. 12, 1992, abandoned.

[51] Int. Cl.$^5$ .............................................. A61N 5/02
[52] U.S. Cl. ........................... 607/99; 607/101; 607/102; 607/116; 604/22; 128/898
[58] Field of Search ..................... 606/39–46; 604/20–22; 607/99–101, 111–118, 153–156; 128/898

[56] References Cited

U.S. PATENT DOCUMENTS

| | | |
|---|---|---|
| Re. 32,066 | 1/1986 | Leveen . |
| 1,879,249 | 9/1932 | Honsaker .................. 604/280 |
| 1,950,788 | 3/1934 | Ewerhardt et al. . |
| 1,968,997 | 8/1934 | Drucker . |
| 2,008,526 | 7/1935 | Wappler et al. . |
| 2,022,065 | 11/1935 | Wappler . |
| 2,047,535 | 7/1936 | Wappler . |
| 2,118,631 | 5/1938 | Wappler . |
| 2,710,000 | 7/1955 | Cramer et al. . |
| 3,230,957 | 1/1966 | Seifert . |
| 3,339,542 | 9/1967 | Howell . |

(List continued on next page.)

FOREIGN PATENT DOCUMENTS

| | | |
|---|---|---|
| A10858/92 | 8/1992 | Australia . |
| 0370890 | 5/1990 | European Pat. Off. . |
| 0453071 | 10/1991 | European Pat. Off. . |
| 0495443 | 7/1992 | European Pat. Off. . |
| 3218314 | 10/1983 | Germany . |
| 2121675 | 5/1990 | Japan . |

(List continued on next page.)

OTHER PUBLICATIONS

Standard Urology Product Catalog, CIRCON ACMI: Stanford (1992).

Chang, Raymond J. et al, American Heart Journal, 125: 1276–1283 (May 1993).

Cosman, Eric R. et al, Sterostatic and Functional Neurosurgery, pp. 2490–2499 (Date Unknown).

Diasonics, Brochure DIA 2000 171 CRF May 1988.

(List continued on next page.)

*Primary Examiner*—C. Fred Rosenbaum
*Assistant Examiner*—Michael Rafa
*Attorney, Agent, or Firm*—Oblon, Spivak, McClelland, Maier & Neustadt

[57] ABSTRACT

A medical probe device comprises a catheter having a stylet guide housing with one or more stylet ports in a side wall thereof and guide means for directing a flexible stylet outward through the stylet port and through intervening tissue at a preselected, adjustable angle to a target tissue. The total catheter assembly includes a stylet guide lumen communicating with the stylet port and a stylet positioned in said stylet guide lumen for longitudinal movement from the port through intervening tissue to a target tissue. The style can be an electrical conductor enclosed within a non-conductive layer, the electrical conductor being a radiofrequency electrode. Preferably, the non-conductive layer is a sleeve which is axially moveable on the electrical conductor to expose a selected portion of the electrical conductor surface in the target tissue. The stylet can also be a microwave antenna. The stylet can also be a hollow tube for delivering treatment fluid to the target tissue. It can also include a fiber optic cable for laser treatment. The catheter can include one or more inflatable balloons located adjacent to the stylet port for anchoring the catheter or dilation. Ultrasound transducers and temperature sensors can be attached to the probe end and/or stylet.

17 Claims, 12 Drawing Sheets

U.S. PATENT DOCUMENTS

| | | |
|---|---|---|
| 3,556,079 | 1/1971 | Omizo .......................... 128/24 AA |
| 3,595,239 | 7/1971 | Petersen ......................... 606/45 |
| 3,598,108 | 8/1971 | Jamshidi et al. . |
| 3,682,162 | 8/1972 | Coyler . |
| 3,828,780 | 8/1974 | Morrison, Jr. . |
| 3,835,842 | 9/1974 | Iglesias . |
| 3,840,016 | 10/1974 | Lindemann . |
| 3,850,175 | 11/1974 | Iglesias . |
| 3,858,577 | 1/1975 | Bass et al. . |
| 3,884,237 | 5/1975 | O'Malley et al. . |
| 3,924,628 | 12/1975 | Droegemueller et al. . |
| 3,939,840 | 2/1976 | Storz . |
| 3,942,530 | 3/1976 | Northeved . |
| 3,948,270 | 4/1976 | Hasson . |
| 3,991,770 | 11/1976 | Leveen . |
| 4,011,872 | 3/1977 | Komiya . |
| 4,119,102 | 10/1978 | Leveen . |
| 4,136,566 | 1/1979 | Christensen . |
| 4,137,920 | 2/1979 | Bonnet . |
| 4,154,246 | 5/1979 | Leveen . |
| 4,204,549 | 5/1980 | Paglione . |
| 4,228,809 | 10/1980 | Paglione ......................... 128/804 |
| 4,267,828 | 5/1981 | Matsuo . |
| 4,295,467 | 10/1981 | Mann et al. . |
| 4,307,720 | 12/1981 | Weber, Jr. . |
| 4,311,145 | 1/1982 | Esty . |
| 4,311,154 | 1/1982 | Sterzer et al. . |
| 4,312,364 | 1/1982 | Convert et al. . |
| 4,375,220 | 3/1983 | Matvias . |
| 4,397,314 | 8/1983 | Vaguine . |
| 4,402,311 | 9/1983 | Hattori . |
| 4,405,314 | 9/1983 | Cope . |
| 4,411,266 | 10/1983 | Cosman . |
| 4,448,198 | 5/1984 | Turner . |
| 4,452,236 | 6/1984 | Utsugi . |
| 4,470,407 | 9/1984 | Hussein ......................... 606/2 |
| 4,494,539 | 1/1985 | Zenitani et al. . |
| 4,552,554 | 11/1985 | Gould et al. ..................... 604/280 |
| 4,562,838 | 1/1986 | Walker . |
| 4,565,200 | 1/1986 | Cosman . |
| 4,568,329 | 2/1986 | Mahurkar ......................... 604/280 |
| 4,580,551 | 4/1986 | Siegmund et al. . |
| 4,594,074 | 6/1986 | Andersen et al. . |
| 4,601,296 | 7/1986 | Yerushalmi . |
| 4,612,940 | 9/1986 | Kasevich et al. . |
| 4,669,475 | 6/1987 | Turner . |
| 4,672,962 | 6/1987 | Hershenson . |
| 4,676,258 | 6/1987 | Inokuchi et al. . |
| 4,681,122 | 7/1987 | Winters et al. . |
| 4,682,596 | 7/1987 | Bales et al. ..................... 606/39 |
| 4,697,595 | 10/1987 | Breyer et al. . |
| 4,700,716 | 10/1987 | Kasevich et al. . |
| 4,706,681 | 11/1987 | Breyer et al. . |
| 4,709,698 | 12/1987 | Johnston et al. . |
| 4,719,914 | 1/1988 | Johnson ......................... 606/45 |
| 4,765,331 | 8/1988 | Petruzzi et al. . |
| 4,769,005 | 9/1988 | Ginsburg et al. . |
| 4,774,949 | 10/1988 | Fogarty . |
| 4,776,086 | 10/1988 | Kasevich et al. . |
| 4,784,638 | 11/1988 | Ghajar et al. . |
| 4,785,829 | 11/1988 | Convert . |
| 4,798,215 | 1/1989 | Turner . |
| 4,800,899 | 1/1989 | Elliott . |
| 4,805,616 | 2/1989 | Pao . |
| 4,813,429 | 3/1989 | Eshel et al. . |
| 4,817,601 | 4/1989 | Roth et al. . |
| 4,818,954 | 4/1989 | Flachenecker et al. . |
| 4,822,333 | 4/1989 | Lavarenne . |
| 4,823,791 | 4/1989 | D'Amelio et al. ............... 606/39 |
| 4,823,812 | 4/1989 | Eshel et al. . |
| 4,860,744 | 8/1989 | Johnson et al. . |
| 4,865,047 | 9/1989 | Chou et al. . |

(List continued on next page.)

FOREIGN PATENT DOCUMENTS

| | | |
|---|---|---|
| WO90/07303 | 7/1990 | WIPO . |
| WO911213 | 8/1991 | WIPO . |
| WO91/16859 | 11/1991 | WIPO . |
| WO92/07622 | 5/1992 | WIPO . |
| WO92/10142 | 6/1992 | WIPO . |
| 9210142 | 6/1992 | WIPO . |
| WO93/25136 | 12/1993 | WIPO . |

OTHER PUBLICATIONS

Perinchery, Narayan, "Neoplasms of the Prostate Gland," pp. 378–397, 408, 409 (Date Unknown).

Urology, 5th Ed., Storz, Jan. 1992.

Transurethral Microwave Thermotherapy For Prostatism: Early Mayo Foundation Experience Michael L. Blute; Mayo Clinic Proceedings; Mayo Clinic, Jacksonville Florida and Minn. vol. 67, May 1992; pp. 417–421.

New Therapies For Benign Prostatic Hyperplasia; Editorial, Dr. R. Bruskewitz et al Mayo Clinic Proceedings Mayo Clinic; vol. 67 pp. 493–495 May 1992.

Industry Strategies, Urology: A Multi Billion Dollar Market . . . Stephen M. Scala et al; Nov. 19, 1991 pp. 1–32.

MMWR Morbidity And Mortality Weekly Report: *Current Trends;* Trends in Prostate Cancer—U.S. 1980–1988, US Department of Health & Human Services, CDC Jun. 12, 1992/vol. 41, No. 23.

U. I. Dept. of Health and Human Servies, MMWR 41: 401–404 vol. 41, No. 23, (Jun. 12, 1992).

U.S. PATENT DOCUMENTS

| Patent No. | Date | Inventor | Class |
|---|---|---|---|
| 4,872,458 | 10/1989 | Kamehira et al. | |
| 4,887,615 | 12/1989 | Taylor . | |
| 4,893,623 | 1/1990 | Rosenbluth . | |
| 4,896,671 | 1/1990 | Cunningham et al. | |
| 4,905,667 | 3/1990 | Foerster et al. | 604/280 |
| 4,907,589 | 3/1990 | Cosman | 606/34 |
| 4,911,148 | 5/1990 | Sosnowski et al. | |
| 4,911,173 | 3/1990 | Terwilliger . | |
| 4,919,129 | 4/1990 | Weber, Jr. et al. | 606/45 |
| 4,920,978 | 5/1990 | Colvin . | |
| 4,932,958 | 6/1990 | Reddy et al. | |
| 4,936,281 | 6/1990 | Stasz . | |
| 4,943,290 | 7/1990 | Rexroth | 606/49 |
| 4,946,449 | 8/1990 | Davis, Jr. . | |
| 4,949,706 | 8/1990 | Thon . | |
| 4,950,267 | 8/1990 | Ishihara et al. | |
| 4,955,377 | 9/1990 | Lennox et al. | |
| 4,961,435 | 10/1990 | Kitagawa et al. | |
| 4,966,597 | 10/1990 | Cosman . | |
| 4,967,765 | 11/1990 | Turner et al. | |
| 4,976,711 | 12/1990 | Parins et al. | |
| 4,998,932 | 3/1991 | Rosen et al. | |
| 4,998,933 | 3/1991 | Eggers et al. | |
| 5,002,558 | 3/1991 | Klein et al. | |
| 5,007,437 | 4/1991 | Sterzer . | |
| 5,007,908 | 4/1991 | Rydell . | |
| 5,010,886 | 4/1991 | Passafaro et al. | |
| 5,026,959 | 6/1991 | Ito et al. | |
| 5,029,588 | 7/1991 | Yock et al. | |
| 5,030,227 | 7/1991 | Rosenbluth et al. | |
| 5,035,695 | 7/1991 | Weber, Jr. et al. | |
| 5,035,696 | 7/1991 | Rydell . | |
| 5,057,105 | 10/1991 | Malone et al. | |
| 5,057,106 | 10/1991 | Kasevich . | |
| 5,059,851 | 10/1991 | Corl et al. | |
| 5,071,418 | 12/1991 | Rosenbaum | 606/45 |
| 5,080,660 | 1/1992 | Buelna . | |
| 5,083,565 | 1/1992 | Parins . | |
| 5,084,044 | 1/1992 | Quint . | |
| 5,100,423 | 3/1992 | Fearnot . | |
| 5,108,415 | 4/1992 | Pinchuk . | |
| 5,109,859 | 5/1992 | Jenkins . | |
| 5,116,615 | 5/1992 | Gokcen et al. | |
| 5,120,316 | 6/1992 | Morales et al. | |
| 5,122,137 | 6/1992 | Lennox | 606/42 |
| 5,135,525 | 8/1992 | Biscoping et al. | |
| 5,150,717 | 9/1992 | Rosen et al. | |
| 5,170,787 | 12/1992 | Lindegren . | |
| 5,178,620 | 1/1993 | Eggers et al. | |
| 5,179,962 | 1/1993 | Dutcher et al. | |
| 5,190,539 | 3/1993 | Fletcher et al. | |
| 5,195,965 | 3/1993 | Shantha . | |
| 5,197,963 | 3/1993 | Parins | 606/41 |
| 5,201,732 | 4/1993 | Parins et al. | |
| 5,220,927 | 6/1993 | Astrahan et al. | |
| 5,228,441 | 7/1993 | Lundquist . | |
| 5,234,004 | 8/1993 | Hascoet et al. | 607/102 |
| 5,235,964 | 8/1993 | Abenaim . | |
| 5,249,585 | 10/1993 | Turner et al. | |
| 5,257,451 | 11/1993 | Edwards et al. | |
| 5,273,524 | 12/1993 | Fox et al. | 606/45 |
| 5,281,218 | 1/1994 | Imran . | |
| 5,300,069 | 4/1994 | Hunsberger et al. | |
| 5,300,099 | 4/1994 | Rudie . | |

MEDICAL PROBE DEVICE AND METHOD

This application is a continuation of application Ser. No. 07/929,638, filed on Aug. 12, 1992, now abandoned.

FIELD OF THE INVENTION

This invention is directed to a unique device and method for penetrating body tissues for medical purposes such as tissue destruction and fluid substance delivery, for example. The device penetrates tissue to the precise target selected in order to deliver energy to the tissue and/or deliver substances. It limits this activity to the precise preselected site, thereby minimizing trauma to normal surrounding tissue and achieving a greater medical benefit. This device is a catheter-like device for positioning a treatment assembly in the area or organ selected for medical treatment with at least one stylet in the catheter, mounted for extension from a stylet port in the side wall of the catheter through surrounding tissue to the tissue targeted for medical activity.

BACKGROUND OF THE INVENTION

Treatment of cellular tissues usually requires direct contact of target tissue with a medical instrument, usually by surgical procedures exposing both the target and intervening tissue to substantial trauma. Often, precise placement of a treatment probe is difficult because of the location of a target tissue in the body or the proximity of the target tissue to easily damaged, critical body organs, nerves, or other components.

Benign prostatic hypertrophy or hyperplasia (BPH), for example, is one of the most common medical problems experienced by middle to older aged men. Urinary tract obstruction due to prostatic hyperplasia has been recognized since the earliest days of medicine. Hyperplastic enlargement of the prostate gland often leads to compression of the urethra, resulting in obstruction of the urinary tract and the subsequent development of symptoms including frequent urination, decrease in urinary flow, nocturia, pain, discomfort, and embarrassment. The association of BPH with aging has been shown to exceed 50% in men over 50 years of age and increases in incidence to over 75% in men over 80 years of age. Symptoms of urinary obstruction occur most frequently between the ages of 65 and 70 when approximately 65% of men in this age group have prostatic enlargement. Currently there is no proven effective nonsurgical method of treatment of BPH. In addition, the surgical procedures available are not totally satisfactory. Currently patients suffering from the obstructive symptoms of this disease are provided with few options: continue to cope with the symptoms (i.e., conservative management), submit to drug therapy at early stages, or submit to surgical intervention. More than 350,000 patients per year undergo surgery for removal of prostatic tissue in the United States.

Those suffering from BPH are often elderly men, many with additional health problems which increase the risk of surgical procedures. Surgical procedures for the removal of prostatic tissue are associated with a number of hazards including anesthesia associated morbidity, hemorrhage, coagulopathies, pulmonary emboli and electrolyte imbalances. These procedures performed currently can also lead to cardiac complications, bladder perforation, incontinence, infection, urethral or bladder neck stricture, retention of prostatic chips, retrograde ejaculation, and impotence. Due to the extensive invasive nature of the current treatment options for obstructive uropathy, the majority of patients delay definitive treatment of their condition. This circumstance can lead to serious damage to structures secondary to the obstructive lesion in the prostate (bladder hypertrophy, hydronephrosis, etc.) which is not without significant consequences. In addition, a significant number of patients with symptoms sufficiently severe to warrant surgical intervention are poor operative risks and are poor candidates for prostatectomy. In addition, younger men suffering from BPH who do not desire to risk complications such as impotence are often forced to avoid surgical intervention. Thus the need, importance and value of improved surgical and non-surgical methods for treating BPH is unquestionable.

High-frequency currents are used in electrocautery procedures for cutting human tissue especially when a bloodless incision is desired or when the operating site is not accessible with a normal scalpel but presents an access for a thin instrument through natural body openings such as the esophagus, intestines or urethra. Examples include the removal of prostatic adenomas, bladder tumors or intestinal polyps. In such cases, the high-frequency current is fed by a surgical probe into the tissue to be cut. The resulting dissipated heat causes boiling and vaporization of the cell fluid at this point, whereupon the cell walls rupture and the tissue is separated. The frequency of the current for this use must be above ca. 300 kHz in order to avoid any adverse such as nerve and/or muscle responses.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using a destructive energy which is rapidly dissipated and reduced to a non-destructive level by conduction and convection forces of circulating fluids and other natural body processes.

Microwave, radiofrequency, acoustical (ultrasound) and light energy (laser) devices, and tissue destructive substances have been used to destroy malignant, benign and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula which is used to carry a radiofrequency electrode or microwave antenna through a duct to the zone of treatment and apply energy diffusely through the duct wall into the surrounding tissue in all directions. Severe trauma is often sustained by the duct wall during this cellular destruction process, and some devices combine cooling systems with microwave antennas to reduce trauma to the ductal wall. For treating the prostate with these devices, for example, heat energy is delivered through the walls of the urethra into the surrounding prostate cells in an effort to kill the tissue constricting the urethra. Light energy, typically from a laser, is delivered to prostate tissue target sites by "burning through" the wall of the urethra. Healthy cells of the duct wall and healthy tissue between the nodules and duct wall are also indiscriminately destroyed in the process and can cause unnecessary loss of some prostate function. Furthermore, the added cooling function of some microwave devices complicates the apparatus and requires that the device be sufficiently large to accommodate this cooling system.

Application of liquids to specific tissues for medical purposes is limited by the ability to obtain delivery without traumatizing intervening tissue and to effect a delivery limited to the specific target issue. Localized chemotherapy, drug infusions, collagen injections, or injections of agents which are then activated by light, heat or chemicals would be greatly facilitated by a device which could conveniently and precisely place a fluid supply catheter opening at the specific target tissue.

OBJECTS AND SUMMARY OF THE INVENTION

It is the principal object of this invention to provide a device and method for penetrating tissue, through intervening tissues to the precise target tissue selected for a medical action such as tissue destruction and/or substance delivery, limiting this activity to the precise preselected site, thereby minimizing the trauma and achieving a greater medical benefit.

One principal object of this invention is to provide a device and method for tissue destruction of body tissues which delivers the therapeutic energy directly into a target tissue while minimizing effects on its surrounding tissue.

Another principal object of this invention is to provide a device and method for introducing fluid treatment agents, particularly flowable liquids, with greater precision and ease to a specific location in the body.

Another object of this invention is to provide a thermal destruction device which gives the operator more information about the temperature and other conditions created in both the tissue targeted for treatment and the surrounding tissue. In addition, it will provide more control over the physical placement of the stylet and over the parameters of the tissue destruction process.

In summary, the medical probe device of this invention comprises a catheter having a control end and a probe end. The probe end includes a stylet guide housing having at least one stylet port in a side wall thereof and guide means for directing a flexible stylet outward through the stylet port and through intervening tissue at a preselected angle to a target tissue. The housing can include an array of such ports. The preselected angle is preferably from 20° to 160° with the central axis of the stylet guide housing. The total catheter assembly includes a stylet guide lumen communicating with the stylet port and a stylet positioned in said stylet guide lumen for longitudinal movement from the port through intervening tissue to a target tissue.

The stylet can be an electrical conductor enclosed within a non-conductive layer, the electrical conductor being an radiofrequency electrode. Preferably, the non-conductive layer is a sleeve which is axially moveable on the electrical conductor to expose a selected portion of the electrical conductor surface in the target tissue. The stylet can also be a microwave antenna.

In a still further embodiment, the stylet is a cannula having an axial treatment fluid supply lumen extending therethrough, and the catheter has a treatment fluid transport lumen communicating with the treatment fluid supply lumen.

An ultrasound transducer can be attached to the probe end or a portion of the stylet for use in positioning the catheter and stylet.

When the stylet includes a radiofrequency electrode or microwave antenna, optimally, at least one temperature sensor such as a thermistor or fiber optic cable can be attached to the probe end, stylet guide housing and/or stylet.

The method of this invention for applying destructive energy to a target tissue comprises first introducing a catheter to a zone adjacent to the tissue to be treated. Then an electrical conductor is moved from the catheter through surrounding tissue into a target tissue to be destroyed. The electrical conductor can be a wire or tube comprising a conductive surface surrounded by a non-conductive sleeve means for preventing significant transfer of energy from the conductor in tissue surrounding the sleeve. Heat is generated in the target tissue from an electric current or electromagnetic field produced by the electrical conductor. Preferably, the volume of tissue being treated is controlled by moving the non-conductive sleeve to expose a selected length of electrode in the body tissue to be treated, the remaining area of the electrode remaining shielded by the sleeve to protect the intervening tissues. The amount and duration of the energy delivery is also varied to control the volume of tissue being treated.

The electrical conductor can be positioned in the tissue to be treated using ultrasound imaging from an ultrasound transducer positioned at a distance from the target tissue or supported by the electrical conductor or non-conducting sleeve.

The extent of heating can be monitored and controlled during the ablative treatment using temperature sensors supported by the electrical conductor or non-conductive sleeve.

DETAILED DESCRIPTION OF THE INVENTION

Figure 1:
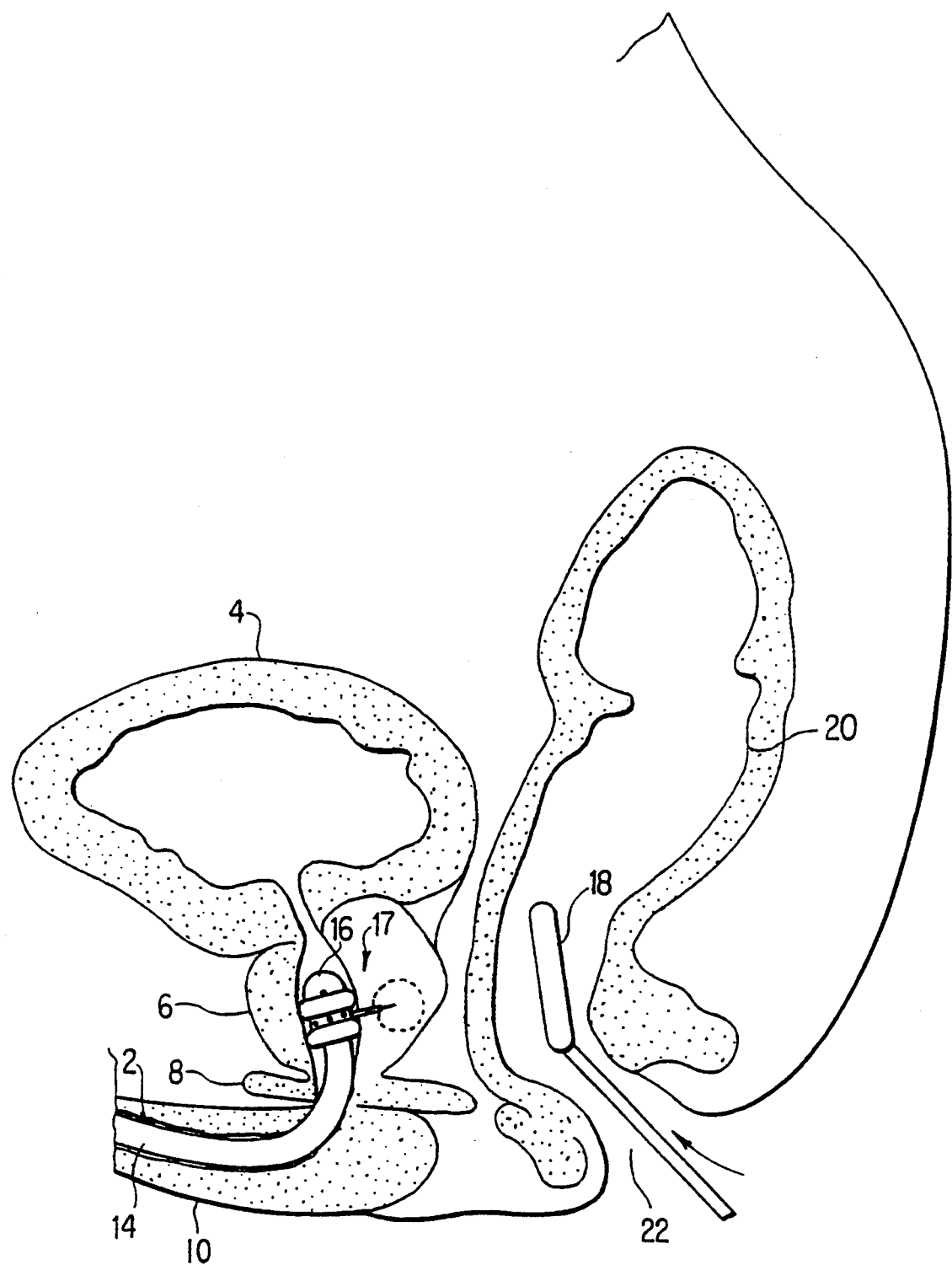
FIG. 1 is a schematic cross-sectional drawing of the lower male anatomy with a device of this invention in position for treatment.

The device of this invention provides a precise controlled positioning of a treatment stylet in a tissue targeted for treatment, destruction or sampling from a catheter positioned in the vicinity of the target tissue.

The term "stylet" as used hereinafter is defined to include both solid and hollow probes which are adapted to be passed from a catheter port through normal tissue to a target tissue. The stylet is shaped to facilitate easy passage through tissue. It can be a solid wire, thin rod, or other solid shape or it can be a thin hollow tube or other shape having a longitudinal lumen for introducing fluids to or removing materials from a site. The styler can also be a thin hollow tube or other hollow shape, the hollow lumen thereof containing a reinforcing or functional rod or tube such as a laser fiberoptic cable. The stylet preferably has a sharpened end to reduce resistance and trauma when it is pushed through tissue to a target site.

The stylet can be designed to provide a variety of medically desired treatments of a selected tissue. As a radiofrequency electrode or microwave antenna, it can be used to ablate or destroy the target tissue. As a hollow tube, it can be used to deliver a treatment fluid such as a liquid to a target tissue. The liquid can be a simple solution or a suspension of solids, for example, colloidal particles, in a liquid. Since the stylet is very thin, it can be directed from the catheter through intervening normal tissue with a minimum of trauma to the normal tissue.

The device and method of this invention provide a more precise, controlled medical treatment which is suitable for destroying cells of medically undesirable tissues throughout the body, both within and external to body organs. The device and method are particularly useful for treating benign prostate hyperplasia (BPH), and the device and its use are hereinafter described with respect to BPH, for purposes of simplifying the description thereof. It will be readily apparent to a person skilled in the art that the device and method can be used to destroy body tissues in areas other than the prostate such as the brain, heart and/or other body cavities and tissue locations that are accessible by percutaneous or endoscopic catheters. Application of the device and method in all of these organs and tissues are intended to be included within the scope of this invention.

BPH is a condition which arises from the benign replication and growth of cells in the prostate, forming glandular and stromal nodules which expand the prostate and constrict the opening of the prostatic urethra. Glandular nodules are primarily concentrated within the transition zone, and stromal nodules within the periurethral region. Traditional treatments of this condition have included surgical removal of the entire prostate gland as well as transurethral resection of the urethral canal and prostate to remove tissue and widen the passageway. One significant and serious complication associated with the latter method is iatrogenic sterility. More recently, laser treatment has been employed to remove tissue, limiting bleeding and loss of body fluids. Balloons have also been expanded within the urethra to enlarge its diameter, with and without destructive heat, but have been found to have significant limitations.

Microwave therapy has been provided with some success by positioning a microwave antenna within the prostatic urethra and generating heat in the tissue surrounding the urethra with a microwave field. Coolants are sometimes applied to reduce the temperature of the urethral wall. This necessitates complicated mechanisms to provide both cooling of the immediately adjacent tissues while generating heat in the more distant prostatic tissue. This technique is similar to microwave hyperthermia. Similarly, radiofrequency tissue destruction with electrodes positioned in the urethra has limited applicability since it necessarily exposes the urethral wall to destructive temperatures.

One embodiment of the device of this invention uses the urethra to access the prostate and positions RF electrode stylets directly into the tissues or nodules to be destroyed. The portion of the stylet conductor extending from the urethra to the target tissue is enclosed within a longitudinally adjustable sleeve shield which prevents exposure of the tissue adjacent to the sleeve to the RF current. Thus the ablative destruction is confined to the tissues targeted for destruction, namely those causing the constriction. Other aspects of the invention will become apparent from the drawings and accompanying descriptions of the device and method of this invention. It will be readily apparent to a person skilled in the art that this procedure can be used in many areas of the body for percutaneous approaches and approaches through body orifices.

FIG. 1 is a schematic cross-sectional drawing of the lower male anatomy during use of the device and method of this invention. The urethra 2 extends from the urinary bladder 4 through the prostate 6, urogenital diaphragm 8 and through the penis 10. BPH is a condition characterized by constriction of the portion of the prostatic urethra caused primarily by proliferation of benign glandular and stroma cells in the prostate. These nodules press the wall of the urethra inwardly, restricting the urethral diameter, and can press normal tissue outwardly, possibly enlarging the prostate. Traditional treatments short of removal of the prostate have included either removal of tissue from the urethra to enlarge its lumen by resection or laser tissue destruction, or by expansion and heating of the tissue surrounding the urethra to a temperature which causes cell death. The latter method is intended to reduce the swelling or enlargement of the prostate, and restore the urethra to at least a portion of its former diameter.

In the method of this invention, a catheter 14 with a stylet guide 16 is passed upwardly through the urethra into the prostate. The position of the guide 16 is precisely controlled, using an ultrasound image, for example, obtained from signals received from the conventional ultrasound transducer 18 inserted into the rectum 20 adjacent to the prostate through the anal opening 22. The guide facilitates easy positioning of the stylet 17 into a precise location under ultrasound imaging.

Figure 2:
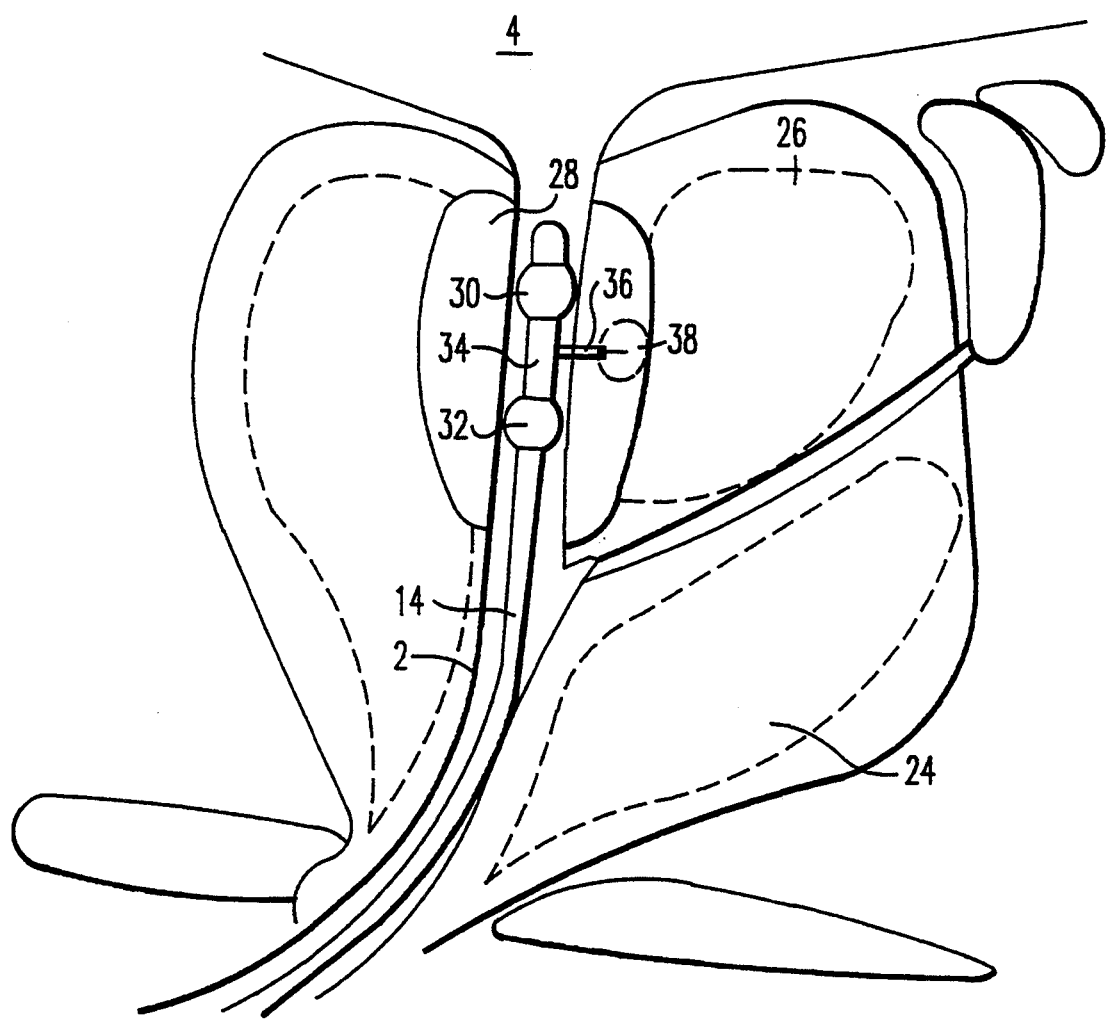
FIG. 2 is a more detailed schematic cross-sectional drawing of the prostate after extension of a stylet into a tissue targeted for destruction.

FIG. 2 is a more detailed schematic cross-sectional drawing of the prostate after extension of an stylet into the transition zone. The prostate comprises the peripheral zone 24, central zone 26 and transitional zone 28. The constrictive cellular nodules of BPH tend to form in the central zone and the transitional zone. Cancer of the prostate is most often found in the peripheral zone 24. The terminal portion of the catheter 14 can have one or more dilation balloons 30 and 32, a stylet guide 34 from which an stylet 36 can be extended until it penetrates a target tissue such as a BPH nodule 38 for treatment.

Figure 4:
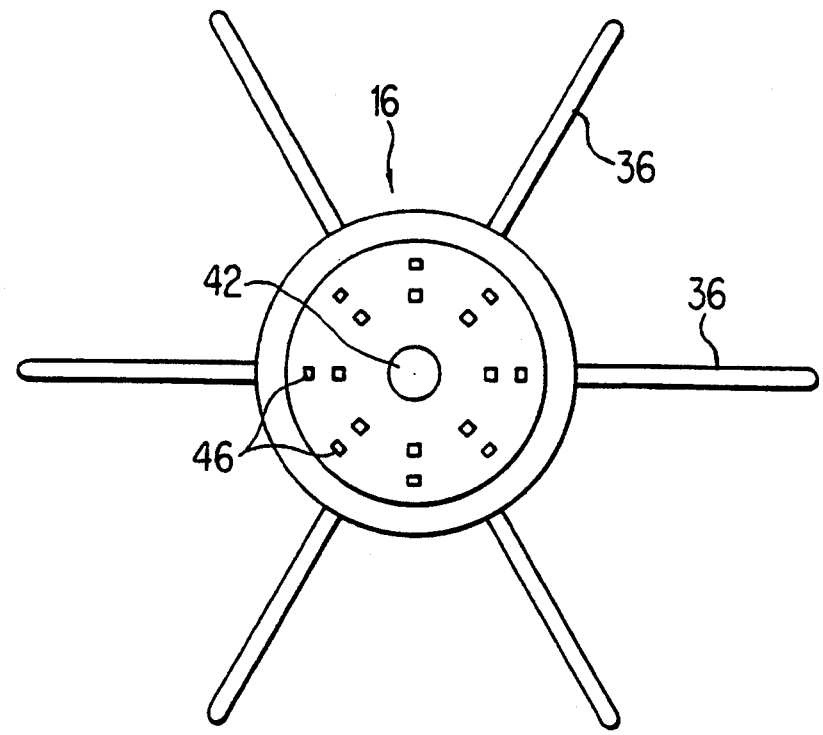
FIG. 4 is an end view of the terminal housing portion shown in FIG. 3.
Figure 3:
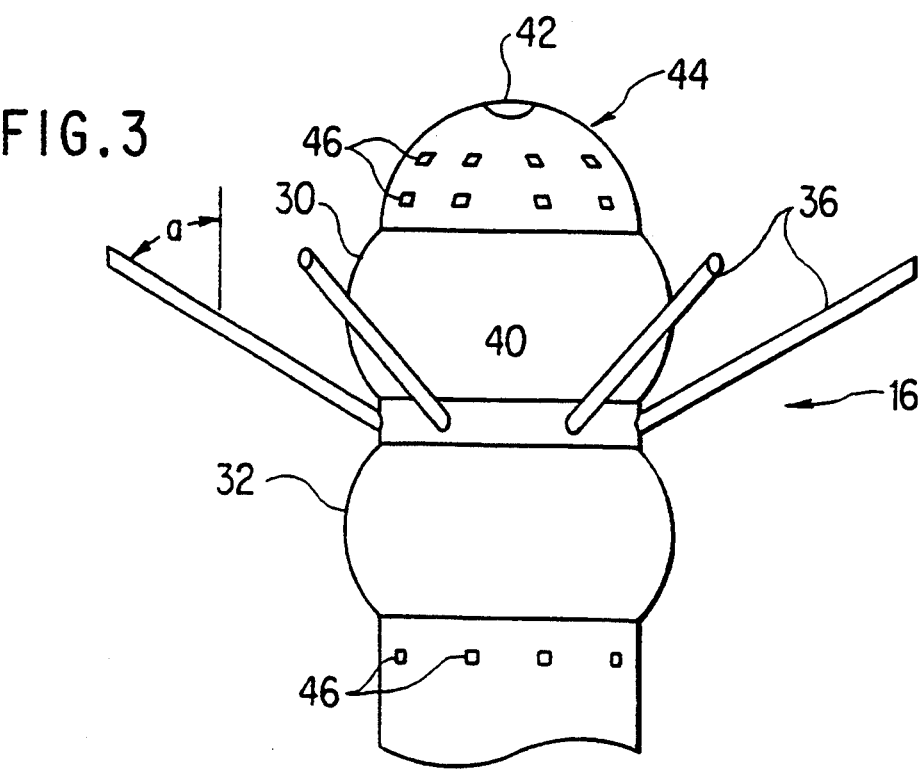
FIG. 3 is a side view of the terminal housing portion of the catheter of this invention with a plurality of extended stylets.

FIG. 3 is a side view and FIG. 4 is an end view of the terminal portion of one embodiment of a catheter of this invention. One or more stylet ports 40 are positioned between the unexpanded annular balloons 30 and 32. An ultrasound transducer 42 can be positioned at the terminal end surface 44 for producing signals and images which can be used for precise positioning of the stylet guide housing 16 in the prostate. One or more temperature sensors 46, which can be conventional thermistors or optical fibers, are positioned along the catheter to provide a temperature profile of the urethra adjacent to and preferably on both sides the stylet section. This temperature profile can be used by the operator to prevent the temperature of the urethral wall from reaching a level which would cause cell destruction. These figures show both balloon segments 30 and 32 and six stylets 36 in an extended position.

The catheter can be rotated about its central axis to orient one or more of the stylets toward tissues to be treated. After the catheter terminal housing 16 is deployed to a treatment position in the prostatic urethra, the annular balloons 30 and 32 can be expanded in the urethra to stabilize the catheter and dilate the urethral lumen. The stylets are extended through the urethral wall and intermediate tissue until they are positioned in the tissue targeted for treatment. The tissue targeted for BPH treatment may be nodules, normal tissue or both. The stylet passageways leading to ports 40 have an orientation such that their terminal axis forms an angle "a" which can be from about 20° to 160° and preferably from about 30° to 150° with the central axis of the catheter in a plane therethrough. As will be explained in greater detail hereinafter with regard to one embodiment of this invention, a non-conducting sleeve is then moved to expose the target tissue to controlled heating by an electric current or an electromagnetic field to a destructive temperature above 45° C. and preferably within the range of from 55° to 99° C.

Figure 5:
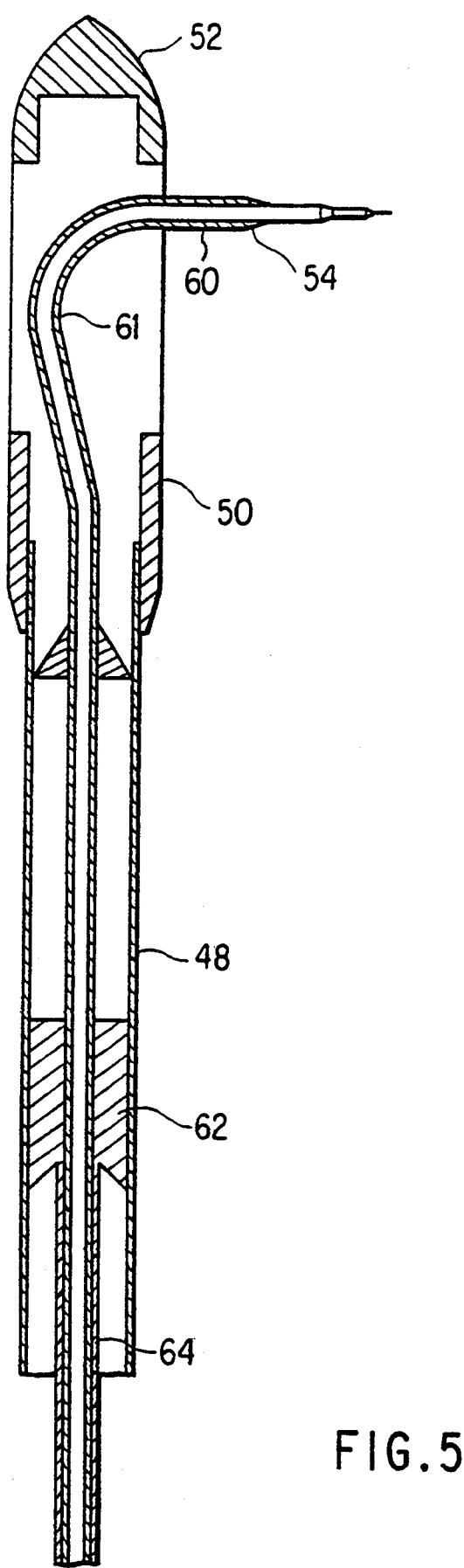
FIG. 5 is a cross-sectional view of an alternative embodiment of the catheter of this invention.
Figure 6:
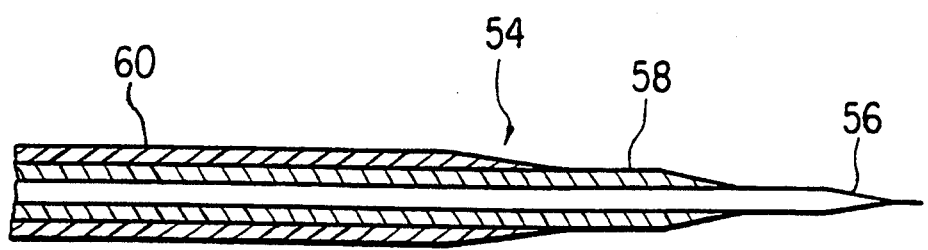
FIG. 6 is a cross-sectional representation of an embodiment of a RF electrode stylet according to this invention.

FIG. 5 is a cross-sectional view of the extended catheter of one embodiment of this invention and FIG. 6 is a cross-sectional enlarged view of the stylet tip shown in FIG. 5. In this embodiment, the catheter 48 is connected to a stylet guide housing 50 with a nose 52. The stylet 54 comprises a solid core needle 56 coaxially positioned within a tube 58, both of which are preferably constructed of a highly flexible, conductive metal such as nickel-titanium alloy. The needle 56 is axially or longitudinally moveable within the tube 58. The tube 58 is enclosed within an non-conductive, non-dielectric sleeve 60 which is longitudinally moveable along the tube. The guide housing 50 has a guide channel 61 which is curved to permit longitudinal advancement of the flexible stylet.

The sleeve 60 is connected to an annular cylinder 62 connected with a longitudinal thrust tube 64. Longitudinal movement of the thrust tube 64 causes a corresponding longitudinal movement of the sleeve 60 along the tube 58. The sleeve movement is used to vary and control the length of tube 58 and needle 56 exposed to surrounding tissue and the resulting volume of tissue exposed to destructive energy. The material, insulating properties, dielectric properties and thickness of the sleeve 60 are selected to prevent heating of tissue in contact therewith by shielding the tissue from the conductor. If the tissue is to be heated using radiofrequency current (300 to 750 kHz, joule or resistive heating), the sleeve 60 must have sufficient thickness required to prevent both current flow and capacitance coupling with the tissue.

Figure 7:
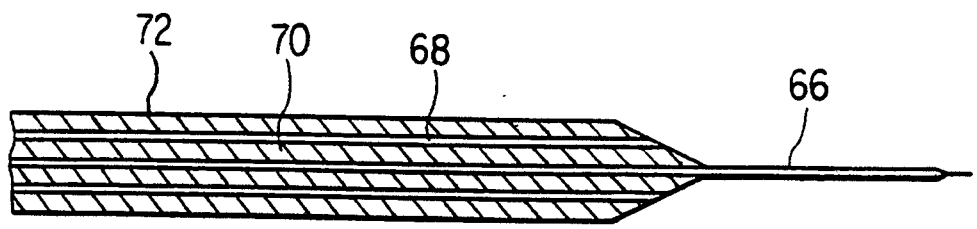
FIG. 7 is a cross-sectional representation of an embodiment of a microwave antenna stylet according to this invention.

FIG. 7 is a cross-sectional representation of an embodiment of a microwave antenna stylet according to this invention. This stylet comprises a coaxial central conductive needle wire 66 concentric with a surrounding conductive wire mesh or tube 68, the space therebetween being filled with a conventional dielectric solid 70. The conductive wire mesh or tube 68 is enclosed within an insulating sleeve or coating 72. After the stylet is advanced into tissue to be treated, electric power is delivered (900 to 2500 MHz), creating a electromagnetic microwave field of destructive energy in the tissue surrounding the needle antenna 66.

Figure 8:
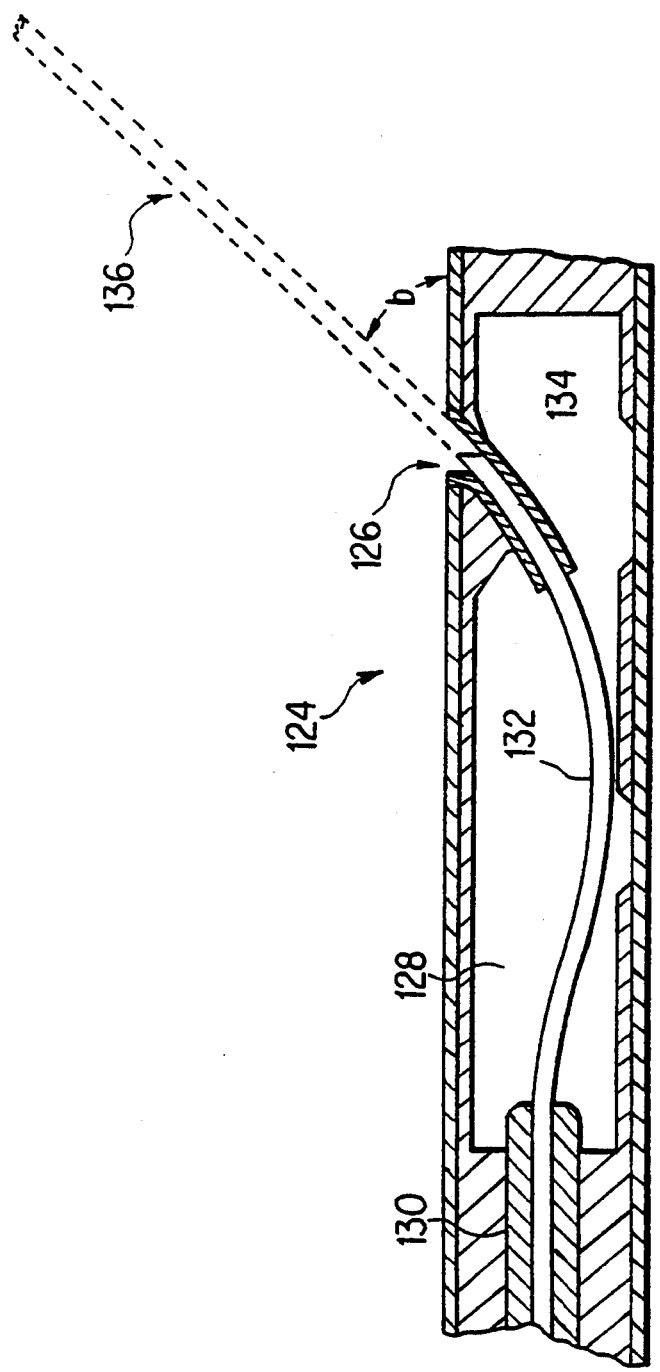
FIGS. 8 and 9 are cross-sectional representations of an embodiment of the catheter of this invention with a styler guide system for adjusting the stylet guide angle.
Figure 9:
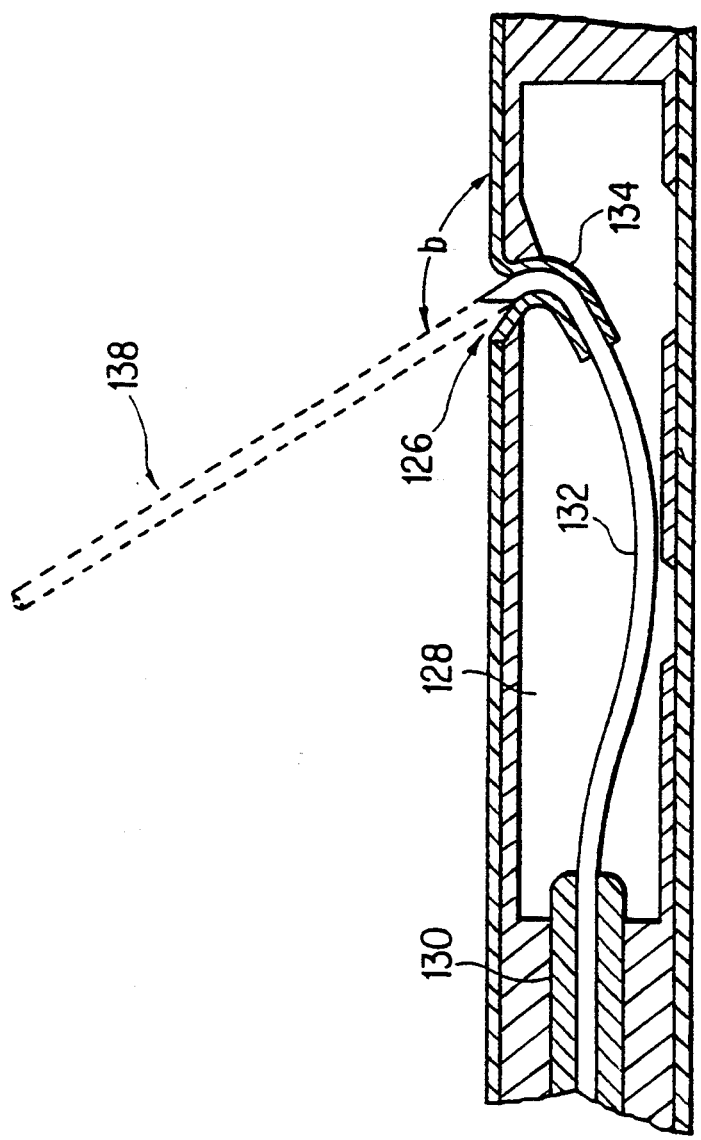

FIGS. 8 and 9 are cross-sectional, fragmentary representations of an embodiment of the catheter of this invention with a stylet guide system for adjusting the stylet guide angle. The stylet guide housing 124 has a stylet port 126. Within the guide housing 124, a stylet positioning block 128 is positioned for axial movement under the action of torque and thrust rod 130. The stylet positioning block 128 has a curved stylet lumen containing the stylet 132. Optionally, a low friction, flexible guide tubing 134 extends from the positioning block 128 to the port 126. In the position shown in FIG. 8, the positioning block 128 is in a retracted position, orienting the stylet to extend at an acute angle "b" of approximately from about 20° and preferably 30° up to 90° with respect to the central axis of the guide housing. Advancement of the styler 132 through the block 128, guide tubing 134 and port 126 directs the stylet into tissue along the dotted line path 136.

Advancement of the positioning block 128 as shown in FIG. 9 forces the stylet 132 through a curved path having a smaller diameter through guide tubing 134 to the port 126. The stylet 132 is then directed an obtuse angle which can be as high as about 160° with respect to the guide housing axis. Advancement of the stylet through the guide block 128, guide tubing 134 and port 126 in this configuration directs the stylet into tissue along the dotted line path 138.

As shown in FIG. 8 and 9, the angular projection of the stylet 132 can be oriented over a wide range of angles in a plane through the central axis of the stylet guide housing. It will be readily apparent that rotation of the torque and thrust rod 130 about its central axis will cause a corresponding rotation of the stylet guide housing and deflection of the stylet in directions outside of the axial plane. This combined with axial movement of the catheter to an optimum position in a duct and rotation of the catheter about its central axis yields an infinite variety of stylet orientation angles. A combination of these movements provides greater choices of stylet angles so that the stylet can be advanced into target tissue at any angle from the catheter.

Figure 10:
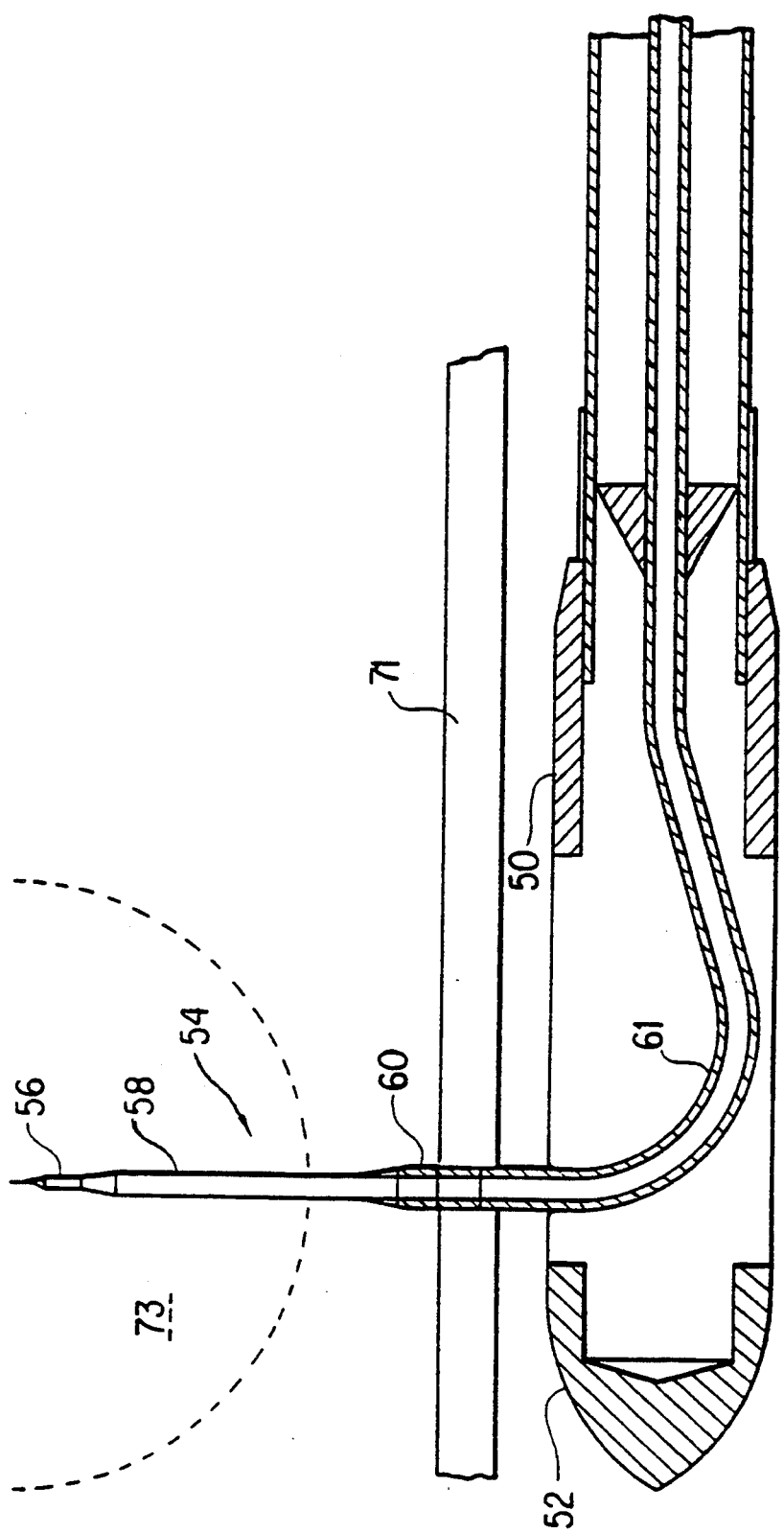
FIGS. 10 and 11 are detailed schematic cross-sectional views of a RF electrode stylet shown in FIGS. 5 and 6 with a partially retracted sleeve positioned to treat tissue targeted for destruction while shielding intervening tissue from treatment according to the method of this invention.
Figure 11:
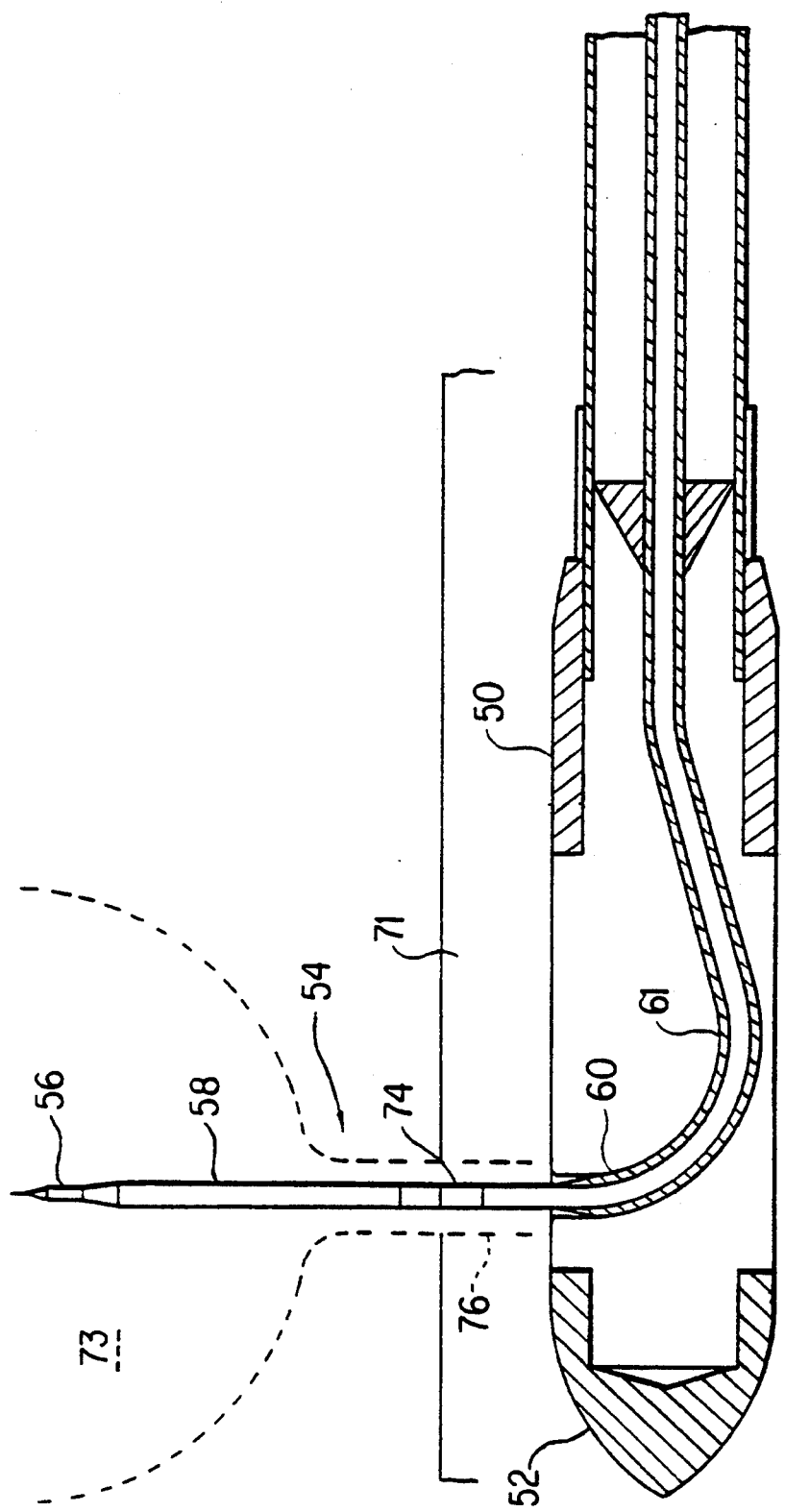

FIGS. 10 and 11 are detailed schematic cross-sectional views of a RF electrode stylet shown in FIGS. 5 and 6 in use. After the catheter is axially positioned in the urethra, the stylet 54 is advanced from the stylet guide housing 50 through the prostatic urethra wall 71 to the target tissue 73 to be treated (outlined with a dotted line). Then, stylet sleeve 60 is retracted to the position shown in FIG. 10, exposing the portion of the RF electrode 56 and 58 positioned immediately in the target tissue 73. RF current is then directed from the electrode 56 and 58 through tissue 73 to conventional grounding plates (not shown). The RF treatment is continued until the cells in the target tissue 73 have been destroyed.

FIG. 11 is a detailed schematic cross-sectional view corresponding to FIG. 10 in an optional second step following the procedure described above. Following destruction of the cells in target tissue 73, the RF electrode sleeve 60 can be retracted along the stylet electrode 58 to the stylet guide housing 50, exposing a length of RF electrode 74 leading from the target tissue through prostatic urethra wall 71. Sufficient RF current is then applied to cauterize the surface of the tissue 76 (shown by dotted lines) immediately in contact with the entire exposed surface of the electrode 58. For example, this can be achieved with a higher voltage and shorter duration treatment than is applied to destroy the cells of the target tissue. The stylet is then fully withdrawn into the housing 50, leaving a drainage duct leading from the area of the target tissue 73 to the prostatic urethra. This can provide drainage of the products of the treated target tissue 73 during the healing process.

The transurethral needle tissue destruction (TUNA) process of this invention is a process whereby a physician in a unique procedure delivers radiofrequency or microwave energy to the hyperplastic nodules of the prostate which develop in men with the condition known as BPH, or Benign Prostatic Hyperplasia. This procedure is unique in that it is the first transurethral procedure which selectively provides the ability to limit the treatment to the nodules and spare the normal prostatic tissue. This procedure also minimizes the trauma sustained by the surrounding prostatic urethra, especially when compared to previously known procedures for relieving obstructive uropathy due to BPH. The procedure could possibly be carried out under local anesthesia only, depending upon the rate of energy delivery and degree of pain sensation experienced by the patient. When local anesthetic is adequate, the procedure can be performed in the physician's office. Local anesthetic could be delivered or applied in the form of a lubricant containing a topical anesthetic such as lidocaine mixed with K-Y jelly.

If substantial pain will be experienced by the patient, the patient must be sedated in addition to application of topical local anesthetic. This procedure can be provided on an outpatient basis and would require a short term (2–6 hour) observation. If the procedure and patient require greater pain control, then spinal anesthesia or a general anesthesia may be used for patients which qualify for their use. This would mandate that the procedure be carried out in the operating room, would require a recovery room, and could possibly require in-patient care in certain circumstances. The previously known prostate resection (TURP) generally requires use of general anesthesia and in-patient hospital care following the treatment.

The BPH method of this invention can be carried out in the following manner, using a RF electrode stylet embodiment of this invention. A male patient is given the appropriate pre-procedure preparation which would usually require a fleets enema or bowel preparation. This would clear the rectal vault of stool in order to better place a rectal ultrasound probe and to assure better visualization. Appropriate anesthetic, if applicable, would then be administered. A conventional grounding plate is then placed in contact with the patient. The rectal probe would then be inserted to the level of the prostate in order to obtain an ultrasound image of the prostate. The urethral catheter would then be inserted in a fashion similar to that used for inserting a Foley catheter. First the glans and the penile shaft would be bathed in betadine or other disinfectant. Then using aseptic or sterile technique, the shaft of the penis is grasped in one hand while the catheter is inserted into the urethral meatus and advanced until it has reached to desired position in the prostatic urethra. The catheter movement during its advancement through the urethra can be monitored directly with the ultrasound image. If this has not been accomplished earlier, the various electrical and mechanical connections between the catheter and the control assembly are connected at this stage.

The RF electrode stylet is then deployed under direct ultrasound imaging into a selected target tissue. This requires that the physician locate the target area to be treated, rotate, advance and/or retract the catheter as necessary to orient the stylet guide port toward the target area. The stylet, preferably completely enclosed in its insulating sleeve or sheath, punctures and penetrates the epithelial lining of the prostatic urethral, traveling through prostatic tissue to the target tissue, and penetrating the tissue to the desired depth. The insulating sleeve is then retracted the amount required to expose a precise selected length of the RF electrode in the target tissue. This amount is selected to effect the degree and volume of tissue destruction desired, the volume increasing as the length of the exposed electrode increases. This volume is selected based on the size of the target tissue to be ablated and the relative position of the electrode stylet in the target tissue. If the sleeve is not clearly visible in the ultrasound image, the distance the sleeve is withdrawn can be measured external to the body using a conventional measuring devices such as a scale.

The electrode stylet is then energized from an RF energy source by closing a conventional switch. Preferably, the time and/or power levels are preset by the control unit. The RF energy is delivered to the target tissue for a preselected time, monitoring the advance of the destructive lesion by the rectal ultrasound image. Impedance is also monitored, and when or if it exceeds a preset value, the power supply can be reduced or terminated. The temperature of the catheter surface adjacent the urethral lining, the sleeve and even the exposed electrode can also be monitored using temperature sensors attached to these components to precisely control the volume of the lesion and prevent excessive heating of normal tissue.

After the target tissue destruction has proceeded to the desired stage, the physician has two options. The stylet electrode can be withdrawn into the catheter to facilitate quick healing and rapid sealing of the urethral puncture site. Alternatively, the physician can create a temporary physiological drainage capillary which would allow any fluid accumulating in the ablated target tissue to drain into the urethra. This physiological drainage capillary can be created after target tissue destruction by withdrawing the insulating sleeve or sheath back into the urethral catheter as shown in FIG. 11. The conductive stylet is then energized to a level sufficient to "sear" or cauterize a small hollow channel through the tissue. This channel will eventually scar and fibrose, or it will seal and heal. The conductive stylet is then entirely withdrawn, and the catheter is slowly and carefully withdrawn from the urethra. The patient is then monitored and treated as appropriate for the type of anesthesia delivered and the condition of the patient.

Figure 12:
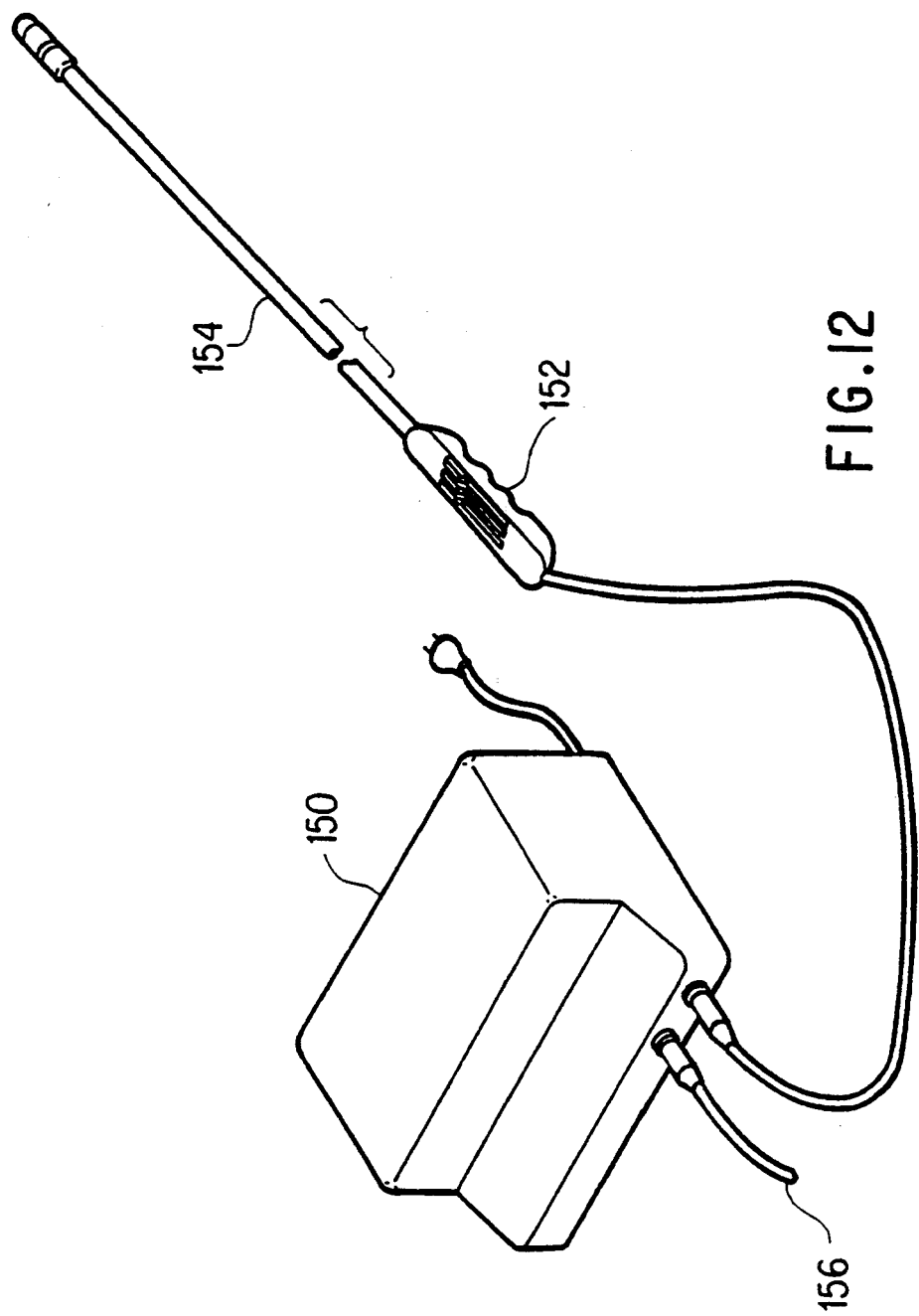
FIG. 12 is a schematic view of the assembly of control unit, manual catheter control unit and catheter according to this invention.

FIG. 12 is a schematic view of the assembly of the power and control console 150, a manual catheter control unit 152, catheter 154, and power foot control 156 according to this invention. The manual operation of the catheter assembly is controlled from a manual control unit shown in greater detail in FIG. 13, with the power control and temperature displays being provided in the control system 150 shown in greater detail in FIG. 14.

Figure 13:
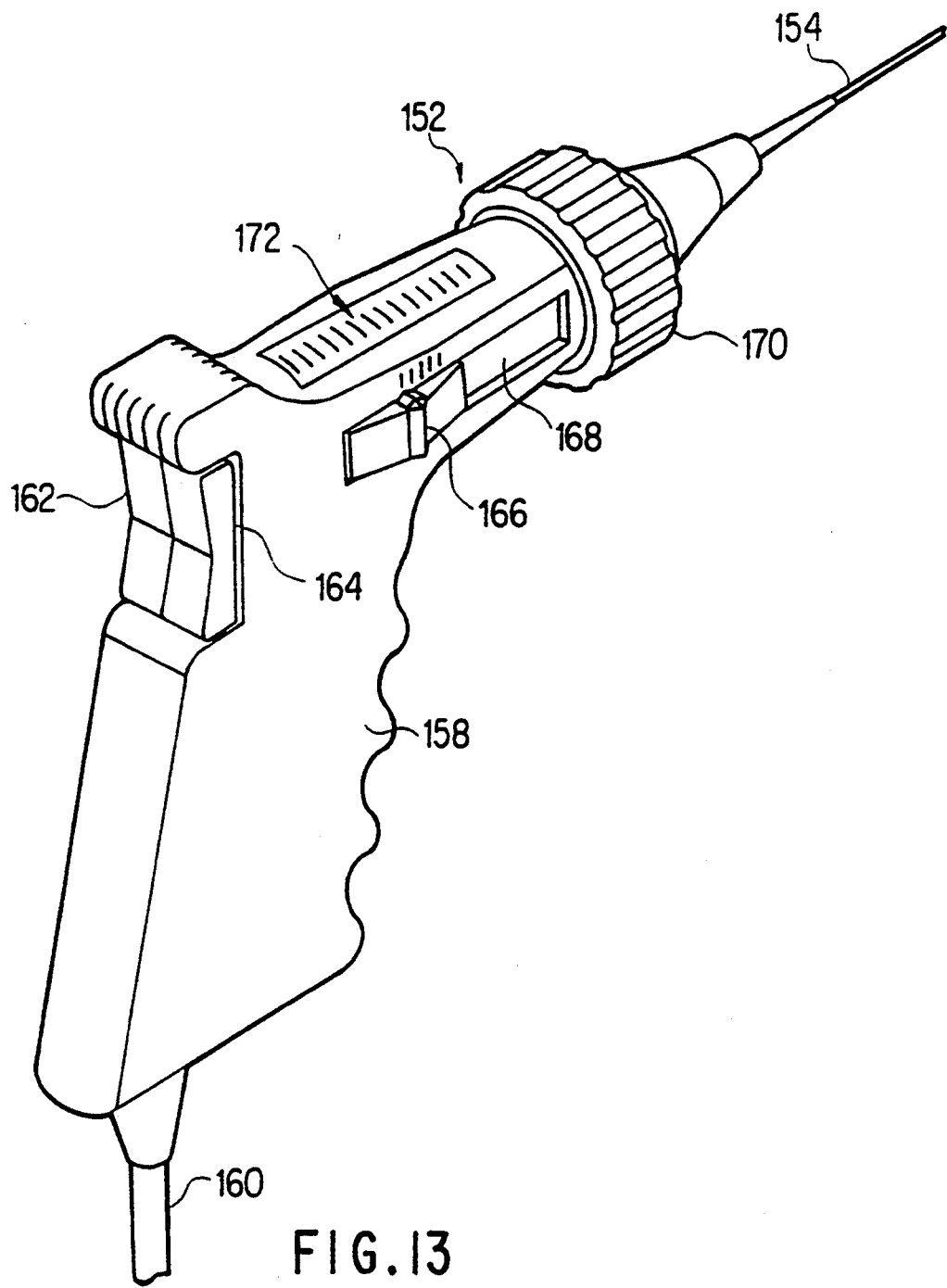
FIG. 13 is an isometric representation of an embodiment of a manual control system of the system of this invention.

FIG. 13 is an isometric representation of an embodiment of a manual control unit of the system of this invention. The manual control unit 152 has a pistol grip 158 with a tube 160 leading to the console shown in FIG. 15. The tube 160 houses RF or microwave power supply cables, temperature sensors, ultrasound transducer power and signal delivery leads, balloon inflation fluid and vacuum lumens.

Rocker switches 162 and 164 provide control over the inflation or deflation of balloons 30 and 32 (FIG. 3). Tab 166 sliding in groove 168 is connected to a stylet 62, advancing it into the a target tissue as the tab 166 is moved forward. Rotary dial 170 is attached to the catheter 154 and can be used to rotate the catheter for orientation of the stylet or stylets. Window 172 has graduations showing the percentage of balloon expansion.

Figure 14:
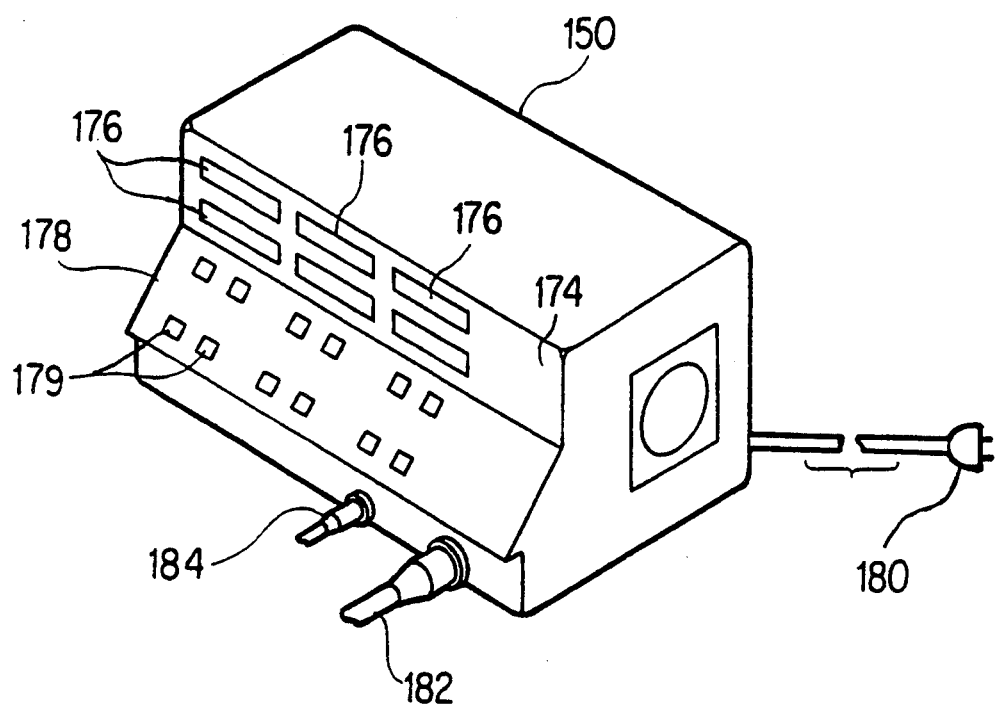
FIG. 14 is an isometric representation of an embodiment of a power and control console of the system of this invention.

FIG. 14 is an isometric representation of an embodiment of a power and control console 150 of the system of this invention. The housing of this console has a display panel 174 with digital readout displays 176 showing power to the stylet, antenna temperatures, tissue temperatures, impedance values, and other data, for example. The housing can support a sealed membrane switch panel 178 having system control buttons 179. Power cord 180 leads to a standard power outlet. Cable 182 leads to the manual catheter control unit 152 shown in FIG. 13. Cable 184 leads to a power foot control unit.

We claim:

1. A method for medical treatment of the prostate, comprising the steps of:
   a) introducing a catheter through the urethra to a zone adjacent to the prostate;
   b) advancing a flexible radio-frequency electrode with a sharpened tip from the catheter through the wall of the urethra into the prostate tissue to be treated, the electrode being retained within an insulating sleeve which is movable relative to the electrode and which sleeve extends through the urethra wall, the sharpened tip puncturing and penetrating the urethra wall;
   c) retracting the insulating sleeve within the prostate tissue to expose a predetermined length of electrode in the prostate tissue; and
   d) passing sufficient electric current through the electrode to raise the temperature of prostate tissue adjacent the predetermined length of electrode to a temperature causing destruction of cells of said prostate tissue.

2. A method of claim 1 wherein the insulating sleeve is axially movable on the electrode, the sleeve being moved axially to define the exposed length of the electrode.

3. A method of claim 1 wherein the electrode, extended into the tissue to be treated, is positioned by use of ultrasound imaging.

4. A method of claim 3 wherein the ultrasound imaging is obtained with an ultrasound transducer positioned on the electrode.

5. A method of claim 1 wherein the catheter is positioned by ultrasound imaging, the ultrasound imaging being obtained with an ultrasound transducer positioned at the end of the catheter.

6. A method of claim 1 wherein the temperature of the target tissue being treated is monitored during the treatment using a temperature sensor attached to the catheter or flexible electrode.

7. A method for medical treatment of the prostate, comprising the steps of:
   a) introducing a catheter through the urethra to a zone adjacent to the prostate;
   b) advancing a flexible radiofrequency electrode with a sharpened tip through a catheter port in the sidewall of the catheter and through the surrounding tissue of the urethra wall into the prostate tissue to be treated, the electrode being retained within an insulating sleeve which is movable relative to the electrode and which sleeve extends through the urethra wall, the sharpened tip puncturing and penetrating the urethra wall;
   c) retracting the insulating sleeve within the prostate tissue to expose a predetermined length of electrode in the prostate tissue; and
   d) passing sufficient electric current through the electrode to raise the temperature of the prostate tissue adjacent the predetermined length of electrode to a temperature causing destruction of cells of said prostate tissue.

8. A method of claim 7 wherein the insulating sleeve is axially movable on the electrode, the sleeve being moved axially to define the exposed length of the electrode.

9. A method of claim 7 wherein the stylet, extended into the tissue to be treated, is positioned by use of ultrasound imaging.

10. A method of claim 9 wherein the ultrasound imaging is obtained with an ultrasound transducer positioned on the electrode.

11. A method of claim 7 wherein the catheter is positioned by ultrasound imaging, the ultrasound imaging being obtained with an ultrasound transducer positioned at the end of the catheter.

12. A method of claim 7 wherein the temperature of the target tissue being treated is monitored during the treatment using a temperature sensor attached to the catheter or flexible electrode.

13. A method for medical treatment of the prostate, comprising the steps of:
   a) introducing a catheter through the urethra to a zone adjacent to the prostate;
   b) advancing a flexible radiofrequency electrode with a sharpened tip through a catheter port in the sidewall of the catheter and through the surrounding tissue of the urethra wall into the prostate tissue to be treated, the electrode being retained with an axially moveable insulating sleeve wherein said sleeve is positioned to enclose a first portion of the electrode which extends through the urethra wall while leaving exposed a second portion of the electrode, said sleeve extending through the urethra wall and the sharpened tip of the electrode puncturing and penetrating the urethra wall;

c) retracting the insulating sleeve within the prostate tissue to expose a predetermined length of electrode in the prostate tissue; and d) passing sufficient electric current through the electrode to raise the temperature of prostate tissue adjacent the predetermined length of electrode to a temperature causing destruction of cells of said prostate tissue.

14. A method of claim 13 wherein the electrode, extended into the tissue to be treated, is positioned by use of ultrasound imaging.

15. A method of claim 14 wherein the ultrasound imaging is obtained with an ultrasound transducer positioned on the electrode.

16. A method of claim 13 wherein the catheter is positioned by ultrasound imaging, the ultrasound imaging being obtained with an ultrasound transducer positioned at the end of the electrode.

17. A method of claim 13 wherein the temperature of the target tissue being treated is monitored during the treatment using a temperature sensor attached to the catheter or flexible electrode.

* * * * *